United States Patent [19]

Kikuchi et al.

[11] Patent Number: 5,124,324
[45] Date of Patent: Jun. 23, 1992

[54] INDOLE DERIVATIVES

[75] Inventors: Haruhiko Kikuchi; Hiroaki Satoh; Makoto Yanai; Toshio Suguro, all of Saitama; Koichiro Hagihara, Kawagoe, all of Japan

[73] Assignee: Nisshin Flour Milling Co., Ltd., Tokyo, Japan

[21] Appl. No.: 614,219

[22] Filed: Nov. 16, 1990

[30] Foreign Application Priority Data

Nov. 17, 1989 [JP] Japan ............... 1-297497

[51] Int. Cl.$^5$ ............... A61K 31/40; A61K 31/445; A61K 31/495; A61K 31/395; C07D 403/00; C07D 401/00; C07D 209/42
[52] U.S. Cl. ............... 514/212; 514/253; 514/323; 514/339; 514/414; 514/415; 514/419; 540/602; 544/238; 544/373; 546/201; 546/273; 548/455; 548/467; 548/468; 548/492
[58] Field of Search ............... 544/238, 373; 546/201, 546/273; 548/455, 467, 468, 492; 514/253, 323, 414, 212, 415, 419, 339; 540/602

[56] References Cited

U.S. PATENT DOCUMENTS

| | | | |
|---|---|---|---|
| 4,486,441 | 12/1984 | Fozard et al. | 546/127 |
| 4,563,465 | 1/1986 | Fozard et al. | 514/304 |
| 4,789,673 | 12/1988 | Donatsch et al. | 514/214 |
| 4,803,199 | 2/1989 | Donatsch et al. | 514/214 |
| 4,910,193 | 3/1990 | Buchheit | 514/216 |
| 4,910,207 | 3/1990 | Donatsch et al. | 514/305 |

FOREIGN PATENT DOCUMENTS

| | | |
|---|---|---|
| 0144986 | 6/1985 | European Pat. Off. |
| 297651 | 1/1989 | European Pat. Off. |
| 307145 | 3/1989 | European Pat. Off. |
| 309423 | 3/1989 | European Pat. Off. |
| 0347229 | 12/1989 | European Pat. Off. |
| 2152049 | 7/1985 | United Kingdom |
| 2193633 | 2/1988 | United Kingdom |
| 8400166 | 1/1984 | World Int. Prop. O. |
| 8502847 | 7/1985 | World Int. Prop. O. |

OTHER PUBLICATIONS

Richardson et al., CA 104-19506g (1986).
Buchheit, CA 113-165432g (1990).
The New England Journal of Medicine, vol. 305, No. 16, Oct. 15, 1981, pp. 905-909, R. J. Gralla et al.
The Lanset, vol. 1, No. 8548, Jun. 27, 1987, pp. 1461-1463, D. Cunningham et al.
Physiological Reviews, vol. 53, No. 1, Jan. 1973, pp. 159-227, A. S. Paintal.
Nature, vol. 316, Jul. 11, 1985, pp. 126-131, B. P. Richardson et al.
Chemical Abstracts, vol. 87, No. 5, 1st Aug. 1977, p. 494, abstract No. 39217x, Columbus, Ohio, US; G. L. Papayan et al.

Primary Examiner—Cecilia Shen
Attorney, Agent, or Firm—Oblon, Spivak, McClelland, Maier & Neustadt

[57] ABSTRACT

Disclosed are compounds of formula I

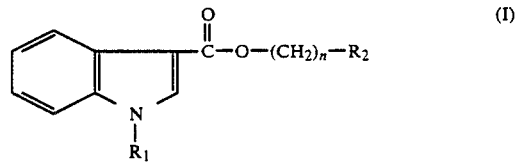

wherein $R_1$ is a hydrogen atom, a $C_1$-$C_6$ alkyl group, benzyl or an indolyl carbonyl group, $R_2$ is a saturated or unsaturated 5- or 8-membered heterocyclic group containing as a hetero atom one or more nitrogen atoms, the heterocyclic group is optionally substituted at an N or C atom by a $C_1$-$C_6$ alkyl or aralkyl group, n is an integer of 1 to 5 and one or more hydrogen atoms, in an alkylene chain —$(CH_2)_n$— are optionally substituted by a $C_1$-$C_6$ alkyl, phenyl and/or hydroxyl group, physiologically acceptable salts and quaternary ammonium salts thereof. The compounds are selective antagonists of 5-HT$_3$ receptors and are useful in the treatment of psychotic disorders, neurotic diseases, gastric stasis symptoms, gastrointestinal disorders, nausea and vomiting.

8 Claims, No Drawings

INDOLE DERIVATIVES

FIELD OF THE INVENTION

This invention relates to indole derivatives, to processes for their preparation and to pharmaceutical compositions comprising them.

In particular the invention relates to compounds which are selective antagonists of 5-hydroxytryptamine (5-HT) at 5-HT$_3$ receptors.

BACKGROUND OF THE INVENTION

Nausea and vomiting are serious problems frequently observed in patients receiving a cancer chemotherapeutic agent and radiotherapy, and control of the nausea and vomiting is a very important auxiliary treatment for undergoing satisfactory treatment for cancer. Since it is reported that intravenous administration of high-dose metoclopramide is effective in inhibition of the vomiting (Gralla, R. J. et al., N. Engl. J. Med. 305, 905–909 (1981)), the vomiting has better, though not perfectly, been controlled. However, it has been revealed that presently available antiemetics, particularly compounds containing a benzamide structure, are associated with adverse reactions such as sedation, ataxia, diarrhea and tasikinesia due to their dopamine-blocking activities and central nerve-depressant activities.

Specific antagonists of 5-HT$_3$ receptors which have recently been reported to inhibit vomiting induced during cancer chemotherapy (Cunningham, D. et al., The Lancet, 1, 1461–1463 (1987)) are considered as a potent antiemetic ones without adverse reactions associated.

Compounds having antagonists activity at 5-HT$_3$ receptors have been described previously. For example U.S. Pat. Nos. 4,486,441; 4,563,465; 4,789,673; 4,803,199 and 4,910,207; UK Patent Specification No. 2152049A and European Patent Specification No. 0309423A2 disclose compounds containing an azabicyclic moiety structure and European Patent Specifications Nos. 0297651A1 and 0307145A1 disclose compounds containing an imidazole ring structure.

Under such circumstances it has been desired to develop selective antagonists of 5-HT at 5-HT$_3$ receptors.

DETAILED DESCRIPTION OF THE INVENTION

We have now found new compounds which differ in structure from the prior compounds and possess a selectively effective antagonism against the effect of 5-HT at 5-HT$_3$ receptors.

According to one aspect of the invention, there are provided compounds of formula (I)

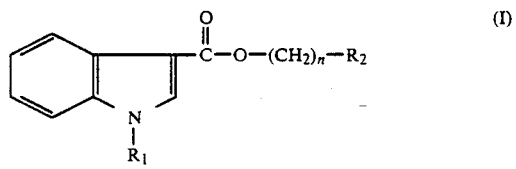

wherein $R_1$ is a hydrogen atom, a $C_1$–$C_6$ alkyl group, benzyl or an indolyl carbonyl group, $R_2$ is a saturated or unsaturated 5- to 8-membered heterocyclic group containing as a hetero atom one or more nitrogen atoms, the heterocyclic group is optionally substituted at an N or C atom by a $C_1$–$C_6$ alkyl or aralkyl group, n is an integer of 1 to 5 and one or more hydrogen atoms in an alkylene chain —$(CH_2)_n$— are optionally substituted by a $C_1$–$C_6$ alkyl, phenyl and/or hydroxyl group, with the proviso of excluding a compound wherein n is 1 and $R_2$ is 1-methyl-2-pyrrolidinyl or 1-benzyl-2-pyrrolidinyl, physiologically acceptable salts and quaternary ammonium salts thereof.

Suitable physiologically acceptable salts of the compounds of formula (I) include acid addition salts formed with organic or inorganic acids, for example, inorganic acid salts such as hydrochloride, hydrobromide, hydroiodide, sulfate and phosphate, and organic acid salts such as oxalate, maleate, fumarate, lactate, malate, citrate, tartrate, benzoate and methanesulfonate. The quaternary ammonium salts include those salts with a lower alkyl halide such as methyl iodide, methyl bromide, ethyl iodide or ethyl bromide, a lower alkylsulfonate such as methyl methanesulfonate or ethyl methanesulfonate or a lower alkyl arylsulfonate such as methyl p-toluenesulfonate. The compounds of formula (I) also include their N-oxide derivatives. Since the compounds of formula (I) and acid addition salts, quaternary ammonium salts and N-oxide derivatives thereof may exist in the form of a hydrate or a solvate, such hydrates and solvates are also included within the scope of the invention.

Compounds of formula (I) that contain at least one asymmetric carbon atom can be present in several stereoisomers. Such stereoisomers and their mixtures and racemates are embraced by the invention.

Examples of the substituents represented by $R_1$ include hydrogen, $C_1$–$C_6$ alkyl such as methyl, ethyl, n-propyl, iso-propyl, n-butyl, iso-butyl, tert-butyl, n-pentyl and n-hexyl, benzyl or indole-3-yl carbonyl. Examples of the heterocyclic group represented by $R_2$ include 1-, 2- or 3-pyrrolidinyl, 1-, 2- or 3-pyrrolyl, 1-, 2-, 4- or 5-imidazolyl, 1-, 3-, 4- or 5-pyrazolyl, 1-, 2-, 3- or 4-piperidyl, 2-, 3- or 4-pyridyl, 1- or 2-piperazinyl, 3- or 4-pyridazinyl, 2-, 4- or 5-pyrimidinyl, hexahydroazepinyl, hexahydrodiazepinyl, octahydroazocinyl, octahydrooctadiazocinyl, etc. Such heterocyclic groups are optionally substituted at an N or C atom by a $C_1$–$C_6$ alkyl group such as methyl, ethyl, n-propyl, iso-propyl, n-butyl, iso-butyl, tert-butyl, n-pentyl or n-hexyl or an aralkyl group such as benzyl, phenethyl or phenylpropyl. The alkylene chain —$(CH_2)_n$— includes methylene, ethylene, propylene, butylene and pentylene, one or more hydrogens of which are optionally substituted by methyl, ethyl, n-propyl, iso-propyl, n-butyl, iso-butyl, tert-butyl, n-pentyl, n-hexyl, phenyl and/or hydroxyl group.

The following compounds illustrate the scope of the compounds of formula (I).

2-(1-Pyrrolidinyl)ethyl 1H-indole-3-carboxylate
2-Piperidinoethyl 1H-indole-3-carboxylate
2-Hydroxy-3-piperidinopropyl 1H-indole-3-carboxylate
(1-Methyl-2-piperidyl)methyl 1H-indole-3-carboxylate
2-(1-Methyl-2-pyrrolidinyl)ethyl 1H-indole-3-carboxylate
(1-Benzyl-2-pyrrolidinyl)methyl 1-(1H-indol-3-yl carbonyl)indole-3-carboxylate
1-(4-Methylpiperidino)-2-propyl 1H-indole-3-carboxylate
1-(4-Methylpiperidino)-2-propyl 1-(1H-indol-3-yl carbonyl)indole-3-carboxylate
1-(2-Methylpiperidino)-2-propyl 1H-indole-3-carboxylate 1-(2-Methylpiperidino)-2-propyl 1-(1H-indol-3-yl carbonyl)indole-3-carboxylate
1-(3-Methylpiperidino)-2-propyl 1H-indoxy-3-carboxylate
1-(3-Methylpiperidino)-2-propyl 1-(1H-indol-3yl carbonyl)indole-3-carboxylate
(1-Methyl-2-piperidyl)methyl 1-methylindole-3-carboxylate
1-(4-Methyl-1-piperazinyl)-2-propyl 1H-indole-3-carboxylate
1-(4-Methyl-1-piperazinyl)-2-propyl 1-(1H-indol-3-yl carbonyl)indole-3-carboxylate
2-(1H-Indole-3-carbonyloxymethyl)-1,1-dimethyl-piperidinium iodide
1,6-Dimethyl-2-piperidylmethyl 1H-indole-3-carboxylate
1,6-Dimethyl-1,2,5,6-tetrahydro-2-pyridylmethyl 1H-indole-3-carboxolyate
(1-Ethyl-2-piperidyl)methyl 1H-indole-3-carboxylate
(1-Ethyl-6-methyl-2-piperidyl)methyl 1H-indole-3-carboxylate
(1-Methyl-2-piperidyl)-1-ethyl 1H-indole-3-carboxylate
(1-Methyl-2-piperidyl)methyl 1-pentylindole-3-carboxylate
(1-Methyl-2-piperidyl)methyl 1-benzylindole-3-carboxylate
(1-Benzyl-2-piperidyl)methyl 1H-indole-3-carboxylate
[1-(2-Propyl)-2-piperidyl]methyl 1H-indole-3-carboxylate
(1-Phenethyl-2-piperidyl)methyl 1H-indole-3-carboxylate
(1-Pentyl-2-piperidyl)methyl 1H-indole-3-carboxylate
(1-Methyl-2-piperidyl)-1-ethyl 1H-indole-3-carboxylate
(1-Methyl-2-piperidyl)-1-ethyl 1H-indole-3-carboxylate
1-(1-Methyl-2-piperidyl)-1-phenylmethyl 1H-indole-3-carboxylate
1-(1-Methyl-2-piperidyl)-2-phenylethyl 1H-indole-3-carboxylate
2-(1-Methyl-2-piperidyl)-2-propyl 1H-indole-3-carboxylate
1-(1-Methyl-2-piperidyl)-1-propyl 1H-indole-3-carboxylate
1-(1-Methyl-2-piperidyl)-2-methyl-1-propyl 1H-indole-3-carboxylate
1-(1-Methyl-2-piperidyl)-1-hexyl 1H-indole-3-carboxylate
(1,4-Dimethyl-2-piperidyl)methyl 1H-indole-3-carboxylate
(1,3-Dimethyl-1,2,5,6-tetrahydro-2-pyridyl)methyl 1H-indole-3-carboxylate
(1,5-Dimethyl-2-piperidyl)methyl 1H-indole-3-carboxylate
(1,3-Dimethyl-2-piperidyl)methyl 1H-indole-3-carboxylate
(1-Methyl-2-hexahydroazepinyl)methyl 1H-indole-3-carboxylate
2-Pyridylmethyl 1H-indole-3-carboxylate
3-Pyridylmethyl 1H-indole-3-carboxylate
4-Pyridylmethyl 1H-indole-3-carboxylate
(S)-(−)-(1-Methyl-2-piperidyl)methyl 1H-indole-3-carboxylate
(R)-(+)-(1-Methyl-2-piperidyl)methyl 1H-indole-3-carboxylate
(1S, 2'S)-(−)-1-(1-Methyl-2-piperidyl)-1-ethyl 1H-indole-3-carboxylate
(1R, 2'R)-(+)-1-(1-Methyl-2-piperidyl)-1-ethyl 1H-indole-3-carboxylate
1,1-Dimethyl-2-(1H-indole-3-carbonyloxymethyl)hexahydroazepinium iodide
1,1-Dimethyl-2-(1H-indole-3-carbonyloxymethyl)-piperidinium bromide
1,1-Dimethyl-2-(1H-indole-3-carbonyloxy-1-ethyl)-piperidinium iodide
1,1-Dimethyl-2-(1H-indole-3-carbonyloxy-1-ethyl)-piperidinium bromide
1,1-Dimethyl-2-(1H-indole-3-carbonyloxymethyl)-piperidinium iodide The compounds of formula (I) can be prepared by a variety of processes, for example by condensation reaction of an indole-3-carboxylic acid or its reactive derivatives of formula (II)

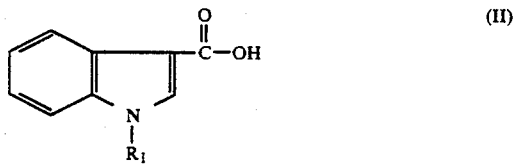

wherein $R_1$ is as defined above, e.g., an indole-3-carboxylic acid halide, particularly indole-3-carboxylic acid chloride with a compound of formula (III)

wherein $R_2$ and n are as defined above.

The reaction can be carried out under various conditions. For example, an acid halide such as indole-3-carboxylic acid chloride is reacted with a compound of formula (III) in an organic solvent such as diethyl ether, diisopropyl ether, tetrahydrofuran, dimethoxyethane, 1,4-dioxane or dimethylformamide at a temperature in the range from −20° C. to a boiling point of the solvent used, if needed in the presence of an inorganic or organic acid-binding agent such as triethylamine, tri-n-butylamine, pyridine, dimethylaniline, tetramethylurea, metallic magnesium, n-butyllithium, lithium diisopropylamide, sodium amide, metallic sodium or sodium hydride. The desired product is obtained via extraction and purification steps following washing of the reaction mixture.

In the case where the compound of formula (III) is a basic compound, an excess amount of the compound may be used for substitution of the acid-binding agent.

Compounds of formula (I), which antagonise the effect of 5-HT at 5-HT$_3$ receptors in the central nervous system, are useful in the treatment of conditions such as psychotic disorders (e.g., schizophrenia, mania, depression, anxiety, dementia, cognitive disorders, dependency on drugs, etc.) and neurotic diseases (e.g., migraine, etc.) or the like. Compounds of formula (I), which antagonise the effect of 5-HT at 5HT$_3$ receptors in the peripheral nervous system, are useful in the treatment of gastric stasis symptoms of gastrointestinal dysfunction such as occur with dyspepsia, reflux oesophagitis, flatulence, and in the treatment of gastrointestinal disorders such as gastritis, peptic ulcer, diarrhea occurred by various causes, Hirschsprung's disease. Compounds of formula (I) are also useful in the treatment of nausea and vomiting, particularly that associated with cancer chemotherapy and radiotherapy.

According to another aspect of the invention, there is provided a pharmaceutical composition having a selective antagonism of 5-HT at 5-HT$_3$ receptors, which comprises as an active ingredient an effective amount of a compound of formula (I), its physiologically acceptable salt or quaternary ammonium salt. Such compositions may be formulated in conventional manner using one or more physiologically acceptable carriers and/or excipients.

The compounds of the invention can usually be administered orally or parenterally in the form of a pharmaceutical formulation. The pharmaceutical formulation includes tablets, capsules, suppositories, troches, syrup, cream, ointment, plasters, cataplasms, granules, powders, injection, suspension and the like. It may be in bilayered or multilayered tablet with other drugs. The tablet may also be coated with a conventional coating to form, for example, sugar-coated, enteric-coated or film-coated tablets.

In preparing the solid formulations, additives such as lactose, refined sugar, crystalline cellulose, corn starch, calcium phosphate, sorbitol, glycin, carboxymethylcellulose, gum arabic, polyvinylpyrrolidone, hydroxypropylcellulose, glycerin, polyethylene glycol, stearic acid, magnesium stearate and talc are employed.

A vegetable or synthetic wax or fat or a similar base is used in preparing the semi-solid formulations.

As additives in preparing the liquid formulations are used, for example, sodium chloride, sorbitol, glycerin, olive oil, almond oil, propylene glycol and ethyl alcohol.

The active ingredient is contained in the formulation in an amount of 0.1–100% by weight, suitably 1–50% by weight in the case of formulations for oral administration and 0.1–10% by weight in the case of formulations for injection based upon the weight of the formulation.

Route and dosage of administration for the compounds of the invention are not specifically limited and are appropriately chosen depending upon form of the formulation, age and sex of the patient, severity of the disease and other factors. Daily dosage of the active ingredient is 1 ng–1000 mg.

The invention is further illustrated by the following non-limitative examples.

EXAMPLE 1

2-(1-Pyrrolidinyl)ethyl 1H-indole-3-carboxylate

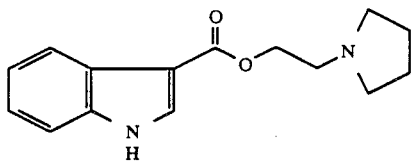

To a dry THF solution of 2-(1-pyrrolidinyl)ethanol (1.10 g, 9.6 mmol) was dropwise added under ice-cooling a 1.5M hexane solution of n-BuLi (6.4 ml, 9.6 mmol) over a period of 10 min. followed by stirring for 30 min. The solvent was removed under reduced pressure. To the residue was added dry THF (20 ml). To the resulting pale yellow suspension was added a dry THF solution (5 ml) of indole-3-carboxylic acid chloride (1.00 g, 5.6 mmol) with stirring at room temperature over a period of 10 min. After stirring overnight, a reaction solution was then concentrated under reduced pressure. The residue was extracted with diluted hydrochloric acid followed by washing with ether. The aqueous layer was adjusted with saturated aqueous sodium bicarbonate to a pH of >10 and again extracted with ether. The organic layer was washed successively with water and saturated aqueous sodium chloride, then dried (MgSO$_4$) and concentrated under reduced pressure to give 1.10 g of the title compound as colorless plates. m.p. 145°–146° C.;

IR$\nu_{max}$(KBr) 3425(w), 2810 (m), 1695(s), 1530(m), 1452(m), 1312(m), 1190 (s), 1055 (m), 758(m) cm$^{-1}$; H-NMR$\delta$ (CDCl$_3$)·1.82(4H, m), 2.71(4H, br. s), 2.96 (2H, t, J=5.9 Hz), 4.50(2H, t, J=5.6 Hz), 7.14–7.19(2H, m), 7.21–7.33(2H, m), 7.70 (1H, d, J=2.9 Hz), 8.08(1H, m); MS(m/z)259 (M$^+$+1, 0.4), 144(100), 116(68), 97(92).

EXAMPLE 2

2-Piperidinoethyl 1H-indole-3-carboxylate

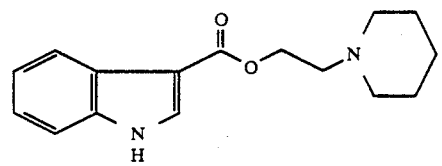

The title compound was prepared by the procedures of Example 1. Prisms; m.p. 123°–125° C.;

IR$\nu_{max}$ (KBr) 3260 (s), 2940(s), 1670(s), 1538(m), 1450(s), 1320(m), 1192(s), 1060(m), 1042(m), 735(s) cm$^{-1}$; H-NMR$\delta$ (CDCl$_3$)1.46(2H, m), 1.62(4H, m), 2.59(4H, m), 2.82(2H, t, J=5.9 Hz), 4.49(2H, t, J=5.9 Hz), 7.10–7.36(4H, m), 7.67(1H, d, J=2.9 Hz), 8.05–8.10(1H, m); MS(m/z)271(M$^+$−1, 0.2), 144(26), 112(80), 98(100).

EXAMPLE 3

2-Hydroxy-3-piperidinopropyl 1H-indole-3-carboxylate

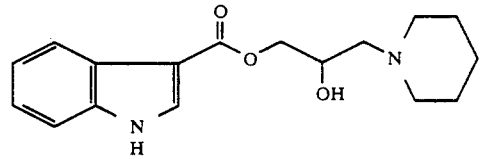

The title compound was prepared by the procedures of Example 1. A foamy solid;

IR$\nu_{max}$ (KBr) 3300(m), 2940(m), 1704(s), 1530(m), 1440(s), 1315(m), 1182 (s), 1048(m), 750(m)cm$^{-1}$; H-NMR$\delta$ (CDCl$_3$) 1.48(2H, m), 1.63(4H, m), 2.45–2.75(6H, m), 4.15–4.40(6H, m), 7.22–7.26(2H, m), 7.41–7.46(2H, m), 7.99(1H, s), 8.11–8.16 (1H, m); MS(m/z)302(M$^+$, 0.2), 144(20), 116 (8), 98(100).

EXAMPLE 4

(1-Methyl-2-piperidyl)methyl 1H-indole-3-carboxylate

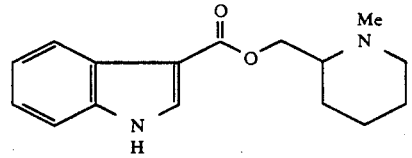

To a THF solution (17 ml) of 1-methyl-2-piperidinemethanol (1.70 g, 13.2 mmol) cooled in an ice-sodium chloride bath to −5° C. was dropwise added a 1.5M hexane solution of n-BuLi (8.7 ml, 13.0 mmol) over a period of 5 min. Stirring was continued under ice-cooling for 30 min. To a mixture was then dropwise added a THF solution (5 ml) of indolecarboxylic acid chloride (1.50 g, 8.35 mmol) over a period of 5 min. After stirring at room temperature for 5 hours, a reaction solution was poured onto diluted hydrochloric acid. The organic layer was separated, and the aqueous layer was extracted with EtOAc. The combined organic layers were then adjusted with saturated aqueous $NaCO_3$ to a pH of >10 and again extracted with EtOAc. The basic extract was washed successively with water and saturated aqueous sodium chloride, then dried over anhydrous magnesium sulfate and concentrated under reduced pressure. The pale yellow crystals thus produced were recrystallized from a chloroform-methanol mixture to give 1.20 g of the title compound as prisms. m.p. 168°–170° C.;

$IR\nu_{max}$(KBr) 2030(m), 2860 (w), 1698(s), 1532(w), 1455(m), 1345(w), 1310 (m), 1179(s), 1025(s) cm$^{-1}$; H-NMRδ (CDCl$_3$)1.25–1.90(6H, m), 2.10–2.50(2H, m), 2.40(3H, s), 2.90(1H, br. d, J=11.5 Hz), 4.38(2H, dq, J=4.6 Hz, J'=11.6 Hz), 7.21(2H, m), 7.45(2H, m), 8.13(1H, m), 11.5(1H, br. s); MS(m/z)144(10), 116(5), 98(100).

EXAMPLE 5

2-(1-Methyl-2-pyrrolidinyl)ethyl 1H-indole-3-carboxylate

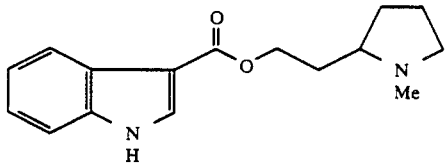

To a dry THF solution (30 ml) of 2-(1-methyl-2-pyrrolidine)ethanol at −10° to 5° C. was dropwise added a 1.5M hexane solution of n-BuLi (16.0 ml, 24.0 mmol) over a period of 10 min. Stirring was continued for 30 min. To a mixture was then dropwise added at −5° to 5° C. a dry THF solution (20 ml) of indole-3-carboxylic acid chloride (4.20 g, 24.0 mmol) over a period of 45 min. The cooling bath was removed. After stirring overnight at room temperature, a reaction solution was poured onto a cold diluted hydrochloric acid, and the aqueous layer was washed with ethyl acetate. The aqueous layer was adjusted with saturated aqueous sodium bicarbonate to a pH of >10 and extracted with ethyl acetate. The organic layer was washed successively with water and saturated aqueous sodium chloride, dried over anhydrous magnesium sulfate and concentrated under reduced pressure to give 1.91 g of the title compound as a yellow viscous material. A foamy solid;

$IR\nu_{max}$(KBr) 2960(m), 1700(s), 1538(m), 1455(m), 1330(w), 1315(w), 1180 (s), 1050(w), 755(m)cm$^{-1}$; H-NMRδ (CDCl$_3$) 1.55–1.90(4H, m), 2.00–2.45(4H, m), 2.40 (3H, s), 3.12(1H, br. t, J=7.0 Hz), 4.40 (2H, t, J=7.9 Hz), 7.22–7.45(4H, m), 7.91 (1H, s), 8.18(1H, m).

EXAMPLE 6

(1-Benzyl-2-pyrrolidinyl)methyl 1-(1H-indol-3-yl carbonyl)indole-3-carboxylate

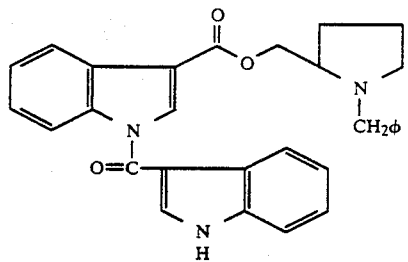

The title compound was prepared by the procedures of Example 1. A yellow viscous material;

$IR\nu_{max}$(film) 3280(w), 2954 (w), 1710(s), 1684(s), 1523(m), 1451(s), 1371(s), 1195(s), 1172(s), 833(s), 750(s) cm$^{-1}$; H-NMRδ (CDCl$_3$) 1.65–1.85 (3H, m), 1.93–2.15(1H, m), 2.20–2.34(1H, m), 2.86–3.08(2H, m), 7.18–7.45(12H, m), 8.05–8.13(1H, m), 8.20–8.28(1H, m), 8.30–8.40 (1H, m), 9.02(1H, br. s); MS(m/z)477(M$^+$, 0.3), 333(0.2), 234(0.4), 160(100).

EXAMPLE 7

1-(4-Methylpiperidino)-2-propyl 1H-indole-3-carboxylate

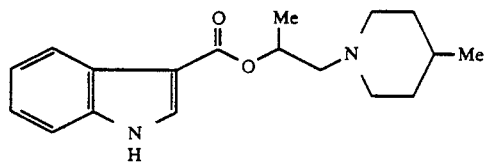

The title compound was prepared by the procedures of Example 1. A colorless viscous material;

$IR\nu_{max}$(film)3290(m), 1700(s), 1676(s), 1534(s), 1453(s), 1377(m), 1177 (s), 788(s)cm$^{-1}$; H-NMRδ (CDCl$_3$) 0.86(3H, d, J=5.9 Hz), 1.15–1.48(3H, m), 1.36(3H, d, J=6.4 Hz), 1.50–1.70(2H, m), 2.00–2.25(1H, m), 2.48 (1H, dd, J=4.4 Hz, J= 13.2 Hz), 2.80–3.20(3H, m), 5.40–5.55 (1H, m), 7.04–7.17(2H, m), 7.20–7.30(1H, m), 7.68(1H, d, 2.4 Hz), 7.85–8.05(1H, m), 9.88(1H, br. s); MS(m/z)301(M$^+$+1, 2), 204 (10), 117(100).

EXAMPLE 8

1-(4-Methylpiperidino)-2-propyl 1-(1H-indol-3-yl carbonyl)indole-3-carboxylate

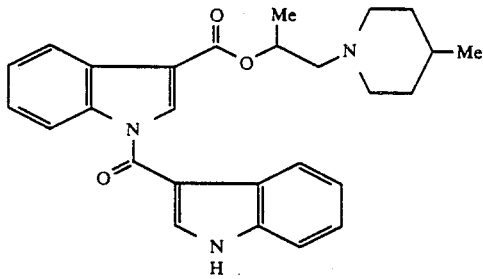

The title compound was prepared by the procedures of Example 1. A pale yellow viscous material;

IRν$_{max}$(film) 1710(s), 1689 (s), 1525(m), 1450(s), 1201(s), 1173(s), 1061(m), 833(s), 790(vs), 763(vs)cm$^{-1}$; H-NMRδ (CDCl$_3$)0.85(3H, d, J=5.9 Hz), 1.08–1.48(3H, m), 1.39(3H, d, J=6.3 Hz), 1.50–1.68(2H, m), 2.00–2.20(2H, m), 2.50(1H, dd, J=4.4 Hz, J=13.2 Hz), 2.74–3.12(3H, m), 5.40–5.55(1H, m), 7.10–7.50(6H, m), 8.05–8.12(2H, m), 8.18–8.30(2H, m), 10.3 (1H. br. s); MS(m/z)445(M$^+$+2, 0.4), 204 (5), 146(100).

EXAMPLE 9

1-(2-Methylpiperidino)-2-propyl 1H-indole-3-carboxylate

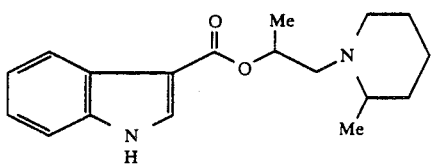

The title compound was prepared by the procedures of Example 1. A pale yellow viscous material;

IRν$_{max}$(film) 2992(m), 1676 (s), 1535(m), 1443(m), 1377(m), 1178(s), 1126(m), 1041(m), 910(m), 789(s), 753(s), 735(s)cm$^{-1}$; H-NMRδ (CDCl$_3$) 1.12–1.16(3H, m), 1.20–1.30(2H, m), 1.36(3H, dd, J=3.4 Hz, 6.4 Hz), 1.45–1.65(3H, m), 2.25–2.55 (3H, m), 2.79(1H, d, J=5.9 Hz), 2.90–3.18 (2H, m), 5.30–5.48(1H, m), 7.16–7.28(2H, m), 7.29–7.40(1H, m), 7.69–7.83(1H, m), 8.09–8.19(1H, m), 9.20–9.60(1H, m); MS (m/z)301(M$^+$+1, 15), 286(20), 202(40), 140 (100).

EXAMPLE 10

1-(2-Methylpiperidino)-2-propyl 1-(1H-indol-3-yl carbonyl)indole-3-carboxylate

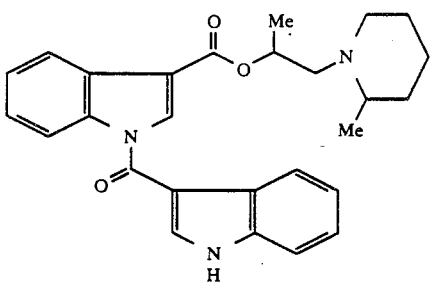

The title compound was prepared by the procedures of Example 1. An orange viscous material;

IRν$_{max}$(film)3296(w), 1684(s), 1525(m), 1451(s), 1440(s), 1383(m), 1201 (s), 1173(s), 834(s), 788(vs), 754(vs) cm$^{-1}$; H-NMRδ (CDCl$_3$) 1.07–1.11 (3H, m), 1.18–1.30(3H, m), 1.39–1.41(3H, m), 1.45–1.80(3H, m), 2.20–2.51(3H, m), 2.70–2.80(1H, m), 2.88–3.10(2H, m), 5.30–5.48 (1H, m), 7.20–7.60(6H, m), 8.07–8.12(1H, m), 8.21–8.26(2H, m), 8.30–8.35(1H, m), 9.58–9.70(1H, m); MS(m/z)444(M$^+$+1, 0.5), 431(1), 202(5), 139(100).

EXAMPLE 11

1-(3-Methylpiperidino)-2-propyl 1H-indole-3-carboxylate

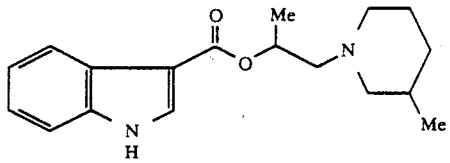

The title compound was prepared by the procedures of Example 1. A pale yellow viscous material;

IRν$_{max}$(film) 1700(s), 1677 (s), 1535(m), 1460(m), 1377(m), 1178(s), 1038(m), 752(s)cm$^{-1}$; H-NMRδ (CDCl$_3$) 0.80–0.88(3H, m), 1.37(3H, d, J=6.3 Hz), 1.45–1.83(5H, m), 1.89–2.13(2H, m), 2.46(1H, dd, J=4.4 Hz, J'=13.2 Hz), 2.77–3.18(3H, m), 5.38–5.53(1H, m), 7.01–7.20(2H, m), 7.21–7.30(1H, m), 7.69(1H, d, J=2.9 Hz), 7.96 (1H, br. d, J=7.8 Hz), 9.82 (1H, br. s); MS(m/z) 302(M$^+$+2, 1.5), 203(3.5), 145 (100).

EXAMPLE 12

1-(3-Methylpiperidino)-2-propyl 1-(1H-indole-3-yl carbonyl)indole-3-carboxylate

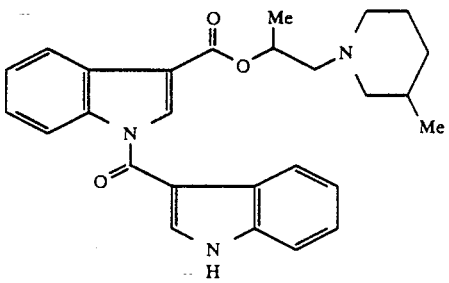

The title compound was prepared by the procedures of Example 1. An orange viscous material;

IRν$_{max}$(film)1686(s), 1551(m), 1526(m), 1450(s), 1370(s), 1202(s), 1175 (s), 1060(m), 833(m), 751(s)cm$^{-1}$; H-NMRδ (CDCl$_3$) 0.79–0.85(3H, m), 1.40(3H, d, J=6.4 Hz), 1.48–1.85(5H, m), 1.88–2.10(2H, m), 2.44–2.53(1H, m), 2.70–3.10(3H, m), 5.40–5.48(1H, m), 7.10–7.50(6H, m), 8.00–8.15(2H, m), 8.18–8.30(2H, m), 10.10(1H, br. s); MS(m/z)444(M$^+$+1, 0.5), 385(1), 203(3.5), 145(100).

EXAMPLE 13

(1-Methyl-2-piperidyl)methyl 1-methylindole-3-carboxylate

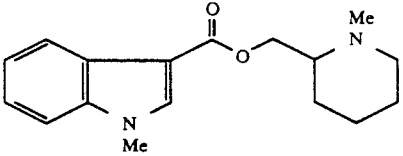

To a DMF (10 ml) suspension of 60% sodium hydride (0.09 g, 2.3 mmol) was dropwise added a DMF (5 ml) solution of (1-methyl-2-piperidyl)methyl 1H-indole-3-carboxylate (0.50 g, 1.8 mmol) at room temperature over a period of 5 min. Onto the reaction mixture stirred for 15 min. was poured a THF (5 ml) solution of methyl iodide (0.29 g, 2.0 mmol). After stirring overnight, a reaction solution was poured onto water followed by extraction with EtOAc. The organic layer was washed successively with water and saturated aqueous sodium chloride, dried over anhydrous sodium sulfate and concentrated under reduced pressure. The crude product thus produced was purified by column chromatography on silica gel (20 g, CHCl₃) to give 0.43 g of the title compound as a colorless oil.

IR$\nu_{max}$(film) 2940(m), 2780(m), 1700(s), 1540(s), 1470(m), 1382 (m), 1268(m), 1226(s), 1105(s), 1018(m), 755(m)cm$^{-1}$; NMR$\delta$ (CDCl₃)1.25–1.90(H, m), 2.06–2.35(2H, m), 2.40(3H, s), 2.80–2.95 (2H, br.), 2.90(2H, m), 3.80(3H, s), 4.38 (2H, dq, J=11.5 Hz, J'=5.1 Hz), 7.30(4H, m), 8.20(1H, m), MS(m/z)287(M+), 158, 111, 98.

EXAMPLE 14

1-(4-Methyl-1-piperazinyl)-2-propyl 1H-indole-3-carboxylate

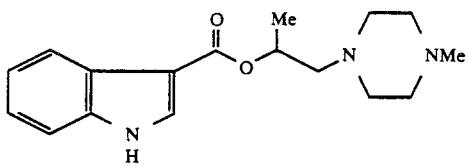

The title compound was prepared by the procedures of Example 1. m.p. 165.5° C.;

IR$\nu_{max}$(KBr)2942(m), 1685(s), 1538(s), 1454(s), 1369(m), 1325(s), 1173 (s), 1115(m), 779(m), 758(m)cm$^{-1}$; H-NMR$\delta$ (CDCl₃)1.39(3H, d, J=6.4 Hz), 2.27(3H, s), 2.30–2.85 (10H, m), 5.32–5.48(1H, m), 7.16–7.25(2H, m), 7.30–7.40(1H, m), 7.81 (1H, d, J=2.9 Hz), 8.08–8.18(1H, m), 9.56 (1H, m); MS(m/z)303(M++2, 4), 202(2), 144 (100).

EXAMPLE 15

1-(4-Methyl-1-piperazinyl)-2-propyl 1-(1H-indol-3-yl carbonyl)indole-3-carboxylate

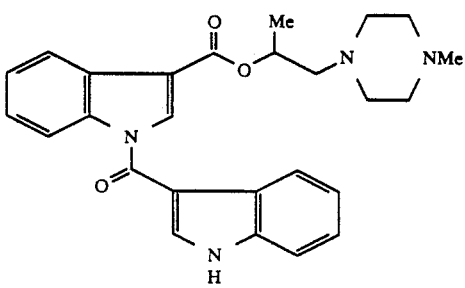

The title compound was prepared by the procedures of Example 1.

H-NMR$\delta$ (CDCl₃) 1.39(3H, d, J=6.4 Hz), 2.26 (3H, s), 2.30–2.80(10H, m), 5.30–5.45(1H, m), 7.28–7.50(5H, m), 7.68(1H, br. s), 8.09–8.13(1H, m), 8.19–8.23(1H, m), 8.28 (1H, s), 8.31–8.36(1H, m), 9.65(1H, br. s); MS(m/z)445(M++1, 0.2), 302(0.3), 243(0.6), 113(100).

EXAMPLE 16

2-(1H-Indole-3-carbonyloxymethyl)-1,1-dimethyl-piperidinium iodide

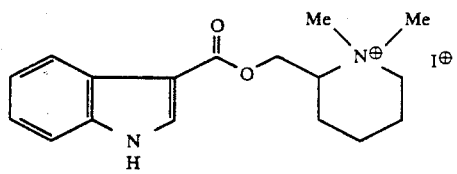

In benzene (10 ml) was dissolved by heating (1-methyl-2-piperidyl)methyl 1H-indole-3-carboxylate (0.10 g, 0.37 mmol) followed by addition of a benzene (5 ml) solution of methyl iodide (0.14 g, 0.99 mmol). The mixture was allowed to react in a stainless steel sealed tube at 100° C. for 2 hours. The reaction tube was cooled, and a reaction product was scraped out by a spatula, washed with IPE and dried (70° C.) under reduced pressure to give 0.11 g of the title compound as a yellow foamy solid. m.p. 95°–97° C.;

IR$\nu_{max}$(KBr)3430(s), 3200(m), 1705(s), 1530(m), 1432(s), 1315(m), 1242(m), 1170 (s), 1124(m), 1042(m), 758(m)cm$^{-1}$; H-NMR$\delta$ (CDCl₃—CD₃OD=1:5)1.65–2.18(6H, m), 3.21 (3H, s), 3.34(3H, s), 3.50–3.62(2H, br.s), 3.80–3.96 (1H, br.), 4.62–4.86(2H, m), 7.22–7.27(2H, m), 7.47–7.51(1H, m), 8.05–8.10(2H, m).

EXAMPLE 17

1,6-Dimethyl-2-piperidylmethyl 1H-indole-3-carboxylate

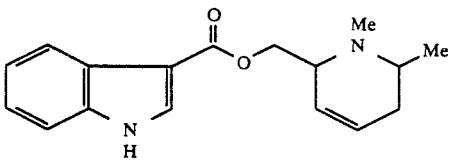

The title compound was prepared by the procedures of Example 1. A foamy solid;

IR$\nu_{max}$(KBr) 2930(s), 2850(m), 1700(s), 1678(s), 1530(m), 1450(s), 1310 (s), 1172(s), 1040(m), 750(s)cm$^{-1}$; H-NMR$\delta$ (CDCl₃) 1.15(3H, d, J=6.2 Hz), 1.30–2.30 (8H, m), 2.45(3H, s), 4.44(2H, d, J=4.4 Hz), 7.15–7.38(3H, m), 7.74(1H, d, J=2.9 Hz), 8.1(1H, m), 9.8(1H, br. s); MS(m/z) 287(M+, 1.6), 144(100), 116(38), 89(44),

EXAMPLE 18

1,6-Dimethyl-1,2,5,6-tetrahydro-2-pyridylmethyl 1H-indole-3-carboxylate

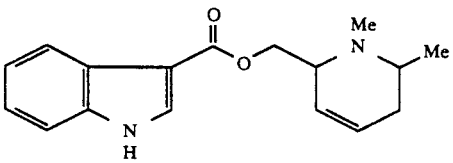

The title compound was prepared by the procedures of Example 1. A foamy solid;

IR$\nu_{max}$(KBr) 2960(w), 1698(s), 1530(m), 1450(m), 1310(w), 1245(w), 1170 (s), 1042(m), 750(s)cm$^{-1}$; H-NMR$\delta$ (CDCl₃) 1.07–1.20 (3H, two d, J=6.8 Hz), 1.82–2.40(3H, m), 2.50–2.57(3H, two s), 3.10–3.50(1H, m), 4.30–4.63(2H, m), 5.51–5.96 (2H, m), 7.20–7.42(3H, m), 7.75(1H, m), 8.14(1H, m), 9.82(1H, br. s); MS(m/z)284 (M+, 5.6), 144(58), 110(100).

EXAMPLE 19

(1-Ethyl-2-piperidyl)methyl 1H-indole-3-carboxylate

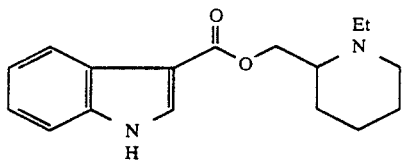

The title compound was prepared by the procedures of Example 1. A foamy solid;
IR$\nu_{max}$(KBr) 3280(w), 2930(m), 1700(s), 1678(s), 1530(m), 1450(m), 1410 (w), 1172(s), 1045(m), 750(s)cm$^{-1}$; H-NMR$\delta$ (CDCl$_3$) 1.09(3H, t, J=7.0 Hz), 1.20–2.20 (6H, m), 2.38(1H, br. q), 2.75(2H, m), 2.90(2H, m), 4.44(2H, dd, J=9.0 Hz, J'=4.7 Hz), 7.21(2H, m), 7.36(1H, m), 7.84(1H, d, J=2.9 Hz), 8.20(1H, m), 9.40(1H, br. s); MS(m/z)287(M+ +1, 0.4), 144(54), 112(100), 89(26).

EXAMPLE 20

(1-Ethyl-6-methyl-2-piperidyl)methyl 1H-indole-3-carboxylate

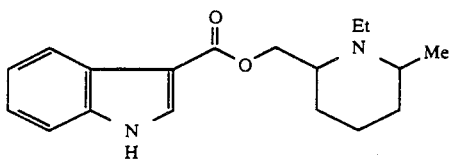

The title compound was prepared by the procedures of Example 1. A foamy solid;
IR$\nu_{max}$(KBr) 2930(s), 1702(s), 1680(s), 1530(m), 1450(m), 1315(w), 1175 (s), 1042(m), 752(m)cm$^{-1}$; H-NMR$\delta$ (CDCl$_3$) 1.00(3H, t, J=7.0 Hz), 1.15(3H, d, J=6.2 Hz), 1.20–2.35(6H, m), 2.57(1H, m), 2.85 (1H, m), 3.05(2H, q, J=6.7 Hz), 4.34(1H, dd, J=5.6 Hz, J'=11.4 Hz), 4.55(1H, dd, J=4.4 Hz, J'=11.0 Hz), 7.25(2H, m), 7.40(1H, m), 7.80(1H, br. d, J=2.1 Hz), 8.19(1H, m), 9.45(1H, br. s); MS(m/z)300(M+, 0.2), 285(76), 144(90), 126(100), 116(38).

EXAMPLE 21

(1-Methyl-2-piperidyl)-1-ethyl 1H-indole-3-carboxylate

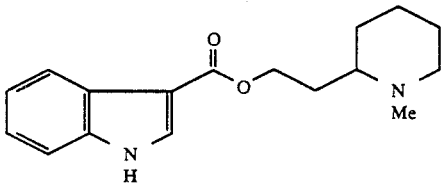

The title compound was prepared by the procedures of Example 1. A foamy solid;
IR$\nu_{max}$(KBr) 3270(w), 2940(s), 2800(w), 1700(s), 1682(s), 1538(s), 1455(m), 1330(w), 1180(s), 1050(m), 758(s) cm$^{-1}$; H-NMR$\delta$ (CDCl$_3$) 1.20–1.95 (6H, m), 2.22(2H, m), 2.37(3H, s), 2.90(1H, br. d, J=11.1 Hz), 4.40(2H, m), 7.25(2H, m), 7.45 (1H, m), 7.91(1H, s), 8.15(1H, m), 9.85(1H, br. s); MS(m/z)286(M+, 0.3), 144(36), 116 (35), 98(100).

EXAMPLE 22

(1-Methyl-2-piperidyl)methyl 1-pentylindole-3-carboxylate

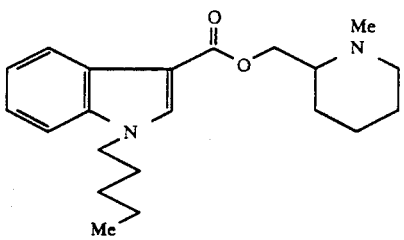

To a DMF (5 ml) suspension of 60% sodium hydride (0.10 g, 2.5 mmol) was dropwise added a DMF (7 ml) solution of (1-methyl-2-piperidyl)methyl 1H-indole-3-carboxylate (0.50 g, 1.7 mmol) at room temperature over a period of 10 min. The mixture was stirred for 45 min., onto which was then poured 1-iodopentane (0.38 g, 1.9 mmol) followed by stirring for additional 4 hours. A reaction solution was poured onto ice water followed by extraction with ethyl acetate (50 ml). The extract was washed successively with water and saturated aqueous sodium chloride and dried over anhydrous magnesium sulfate. The solvent was removed under reduced pressure to give a pale yellow crude product (0.52 g). Purification of the product by column chromatography on silica gel (SiO$_2$: 20 g, CHCl$_3$/MeOH=20/1) afforded the title compound (0.33 g) as a colorless oil.
$^1$H-NMR (CDCl$_3$) $\delta$ 0.89(t, J=6.4 Hz, 3H), 1.20–1.95 (m, 12H), 2.08–2.45(m, 2H), 2.42(s, 3H), 2.88 (br. d, J=11.2 Hz, 1H), 4.13(t, J=7.1 Hz, 2H), 4.30(dd, J=4.9 Hz, J'=11.5 Hz, 1H), 4.46(dd, J=4.9 Hz, J'=11.5 Hz, 1H), 7.23–7.38(m, 3H), 7.84(s, 1H), 8.16 (m, 1H); IR (film) 2930, 1700, 1538, 1470, 1400, 1225, 1185, 1112, 752 cm$^{-1}$; Mass (m/e) 343(M+, 3), 214(55), 144(45), 111 (100).

EXAMPLE 23

(1-Methyl-2-piperidyl)methyl 1-benzylindole-3-carboxylate

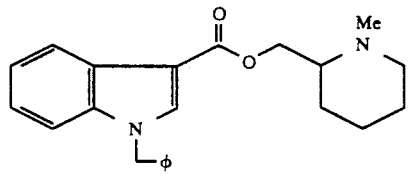

The title compound was prepared by the procedures of Example 22.
$^1$H-NMR(CDCl$_3$)$\delta$ 1.20–1.90 (m, 6H), 2.05–2.35(m, 2H), 2.41(s, 3H), 2.90(d, J=13.2 Hz, 4H), 4.32(dd, J=4.9 Hz, J'=11.2 Hz, 1H), 4.47(dd, J=4.6 Hz, J'=11.5 Hz, 1H), 5.33(s, 3H), 7.12–7.16(m, 2H), 7.23–7.35(m, 6H), 7.88(s, 1H), 8.21(br. d, J=7.3 Hz, 1H); IR (film) 2940, 1700, 1538, 1462, 1395, 1240, 1180, 1092, 752 cm$^{-1}$; Mass(m/e) 363(M+, 1), 234(27), 204(12), 111(100).

EXAMPLE 24

(1-Benzyl-2-piperidyl)methyl 1H-indole-3-carboxylate

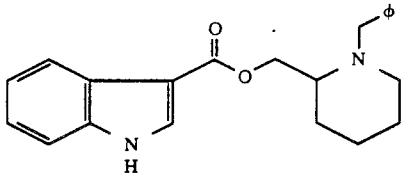

The title compound was prepared by the procedures of Example 1 using 1-benzyl-2-piperidinemethanol prepared in Reference Example 3.

$^1$H-NMR(CDCl$_3$) δ 1.30–1.93(m, 5H), 2.04–2.19(m, 1H), 2.78(m, 2H), 3.38(d, J=13 Hz, 1H), 4.17(d, J=13 Hz, 1H), 4.50(m, 2H), 7.16–7.42(m, 8H), 7.90(d, J=3 Hz, 1H), 8.21(m, 1H), 8.81(br, s, 1H); IR (film) 3296, 2934, 1678, 1534, 1442, 1313, 1244, 1172, 1126, 1047, 752 cm$^{-1}$.

EXAMPLE 25

[1-(2-Propyl)-2-piperidyl]methyl 1H-indole-3-carboxylate

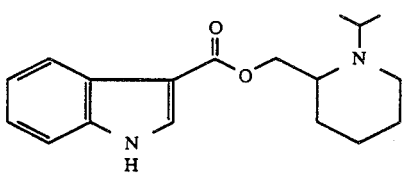

The title compound was prepared by the procedures of Example 1 using 1-(2-propyl)-2-piperidinemethanol prepared in Reference Example 4.

$^1$H-NMR(CDCl$_3$)δ 0.99, 1.17(two d, J=7 Hz, 3H×2), 0.85–1.94(br., 5H), 2.20(m, 1H), 2.88(br. s, 2H), 3.47(m, 1H), 4.33(dd, J=14 Hz, J'=3H, 1H), 4.51(dd, J=14 Hz, J'=3H, 1H), 7.15–7.46(m, 3H), 7.91(d, J=3 Hz, 1H), 8.20(m, 1H), 8.90(br. 1H); IR (film) 3270, 2932, 1679, 1533, 1444, 1314, 1174, 1044, 779, 752 cm$^{-1}$.

EXAMPLE 26

(1-Phenethyl-2-piperidyl)methyl 1H-indole-3-carboxylate

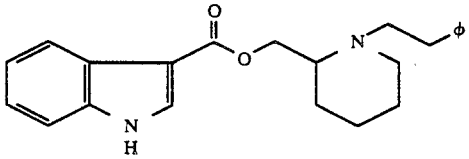

The title compound was prepared by the procedures of Example 1 using 1-(1-phenethyl)-2-piperidinemethanol prepared in Reference Example 4.

$^1$H-NMR(CDCl$_3$) δ 1.30–1.93(m, 8H), 2.40–2.55(m, 1H), 2.75–3.08(m, 4H), 4.38(dd, J=5.1 Hz, 1H), 4.57(dd, J=5.1 Hz, 1H), 7.12–7.32(m, 8H), 7.38–7.42(m, 1H), 7.84(d, J=3 Hz, 1H), 8.13–8.23(m, 1H), 8.83(br. s, 1H); IR(KBr) 2934, 1679, 1533, 1444, 1313, 1173, 1125, 1045, 752 cm$^{-1}$; MS(m/e) 363 (M+1), 252(92), 146(80).

EXAMPLE 27

(1-Pentyl-2-piperidyl)methyl 1H-indole-3-carboxylate

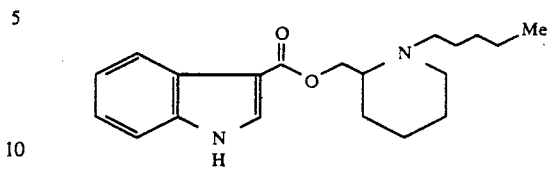

The title compound was prepared by the procedures of Example 1 using 1-pentyl-2-piperidinemethanol prepared in Reference Example 4.

$^1$H-NMR (CDCl$_3$) δ 0.84(t, J=6.5 Hz, 2H), 1.18–1.35(m, 3H), 1.43–1.93(m, 10H), 2.25–2.42(m, 1H), 2.48–2.98(m, 4H), 4.43 (m, 1H), 4.45(m, 1H), 7.21–7.29(m, 2H), 7.35–7.43(m, 1H), 7.86(d, J=2.9 Hz, 1H), 8.13–8.21(m, 1H), 9.32(br. s, 1H); IR (KBr) 2934, 1683, 1536, 1217, 1173, 758 cm$^{-1}$

EXAMPLE 28

(1-Methyl-2-piperidyl)-1-ethyl 1H-indole-3-carboxylate

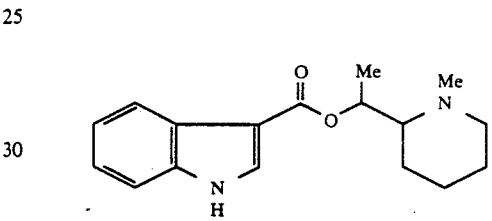

To an ice-cooled solution of (1-methyl-2-piperidyl)-1-ethanol (19.4 g, 140 mmol), obtained according to the procedures in Reference Example 4 starting with pyridine-1-ethanol, and 1,3-dimethyl-2-imidazolidinone (30 ml, 270 mmol) in THF (300 ml) was dropwise added 1.6M hexane solution of n-butyllithium (85 ml, 140 mmol) over a period of 25 min. After stirring for 30 min., a THF (100 ml) solution of indole-3-carboxylic acid chloride (17.0 g, 95 mmol) and 1,3-dimethyl-2-imidazolidinone (10 ml, 90 mmol) was added at a temperature of −5° C. or below over a period of 50 min. The mixture was stirred under cooling for 30 min. followed by removal of the ice bath and stirring for additional one hour. A reaction mixture was poured onto water (500 ml) followed by extraction with ethyl acetate (500 ml). The organic layer was washed with water and then transferred to diluted hydrochloric acid (500 ml). The acid layer was washed with ethyl acetate, adjusted with sodium carbonate to a pH >10 and extracted with ethyl acetate (3×200 ml). The organic layer was washed successively with water and saturated aqueous sodium chloride and then dried over anhydrous magnesium sulfate. The solvent was removed by distillation under reduced pressure to give a crude product (9.5 g) as a yellow oil, which was found by NMR to be an approximately 5:1 diastereomeric mixture. Thus, the oil was crystallized from a chloroform-isopropyl ether to afford a less polar major product as colorless crystals, which were a single diastereoisomer of the title compound (6.10 g). m.p. (HCl salt): 185° C.

$^1$H-NMR(CDCl$_3$) δ 1.20–1.97(m, 6H), 1.37 (d, J=7 Hz, 3H), 2.05–2.40(m, 2H), 2.36(s, 3H), 2.83–2.95(m, 1H), 5.56–5.68(m, 1H), 7.20–7.34(m, 2H), 7.35–7.46(m, 1H), 7.93 (d, J=3H, 1H), 8.12–8.23(m, 1H), 8.60–8.85(br., 1H); IR (KBr) 3070, 2950, 2600, 1700, 1520, 1440, 1320, 1180, 1110, 1030, 780 cm$^{-1}$.

EXAMPLE 29

(1-Methyl-2-piperidyl)-1-ethyl 1H-indole-3-carboxylate

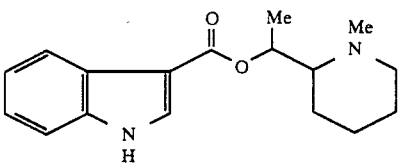

The mother liquor from the crystallization in Example 28 was concentrated. The residue (3.20 g) which contained a more polar diastereomer in a higher proportion was purified by a column chromatography on silica gel (SiO$_2$:60 g, chloroform:methanol=20:1) to give a single substance of the more polar diastereoisomer as a colorless oil.

$^1$H-NMR(CDCl$_3$) δ 1.36(d, J=6.5 Hz, 3H), 1.20–1.50(br. m, 2H), 1.60–1.85(br., 2H), 1.85–2.05(br. m, 2H), 2.22(br. d, J=10.6 Hz, 2H), 2.54(s, 3H), 3.03(br. d, J=10.9 Hz, 1H), 5.62(dd, J=6.5 Hz, J'=1.7 Hz, 1H), 7.00–7.12(m, 2H), 7.25(m, 2H), 7.71(s, 3H), 7.94(m, 1H), 10.8(br., 1H).

EXAMPLE 30

1-(1-Methyl-2-piperidyl)-1-phenylmethyl 1H-indole-3-carboxylate

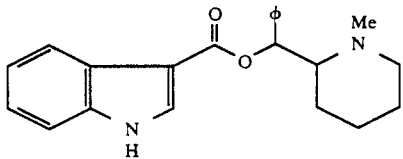

The title compound was prepared by the procedures of Example 1 using (1-methyl-2-piperidyl)-1-phenylmethanol prepared in Reference Example 6.

m.p. 252°–253° C.

$^1$H-NMR(CDCl$_3$) δ 1.20(m, 2H), 1.54(m, 4H), 2.40(m, 1H), 2.60(s, 3H), 2.80(m, 1H), 2.97(m, 1H), 6.39(d, J=6 Hz, 1H), 7.28(m, 9H), 7.93(m, 1H), 8.20(m, 1H); IR (KBr) 3400, 3310, 3130, 3100, 2940, 2800, 1700, 1625, 1585, 1460, 1380, 1315, 1250, 1125, 1110, 1045, 760 cm$^{-1}$.

EXAMPLE 31

1-(1-Methyl-2-piperidyl)-2-phenylethyl 1H-indole-3-carboxylate

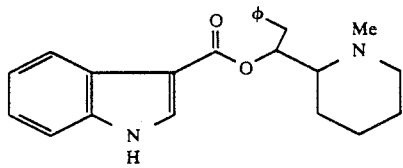

The title compound was prepared by the procedures of Example 1 using 1-(1-methyl-2-piperidyl)-2-phenylethanol prepared in Reference Examples 5 and 6.

m.p. 245°–248° C.

$^1$H-NMR(CDCl$_3$)δ 1.60(br. m, 6H), 2.17(m, 2H), 2.53(s, 3H), 2.94(dd, J=7 Hz, J'=14 Hz, 2H), 3.15(dd, J=8 Hz, J'=14 Hz, 1H), 5.85(t, J=7 Hz, 1H), 6.90(dd, J=7 Hz, J'=15 Hz, 1H), 7.18(dd, J=6 Hz, J'=15 Hz, 1H), 7.25(m, 6H), 7.58(d, J=3 Hz, 1H), 7.77(d, J=7 Hz, 1H); IR (film) 3300, 3030, 2940, 1860, 1700, 1630, 1610, 1585, 1540, 1460, 1380, 1340, 1270, 1220, 1180, 1125, 1090, 990, 750 cm$^{-1}$.

EXAMPLE 32

2-(1-Methyl-2-piperidyl)-2-propyl 1H-indole-3-carboxylate

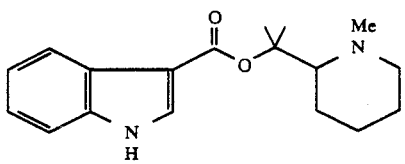

The title compound was prepared by the procedures of Example 1 using 1-(1-methyl-2-piperidyl)-2-propanol prepared in Reference Examples 5 and 6.

$^1$H-NMR(CDCl$_3$)δ 1.32(m, 2H), 1.57(br. m, 2H), 1.65(s, 3H), 1.70(s, 3H), 1.81(m, 2H), 2.30(m, 1H), 2.45(s, 3H), 2.87(m, 2H), 3.08(m, 1H), 7.26(m, 2H), 7.37(m, 1H), 7.81(d, J=3 Hz, 1H), 8.18(m, 1H), 9.78(br. s, 1H); IR (film) 3300, 3020, 1680, 1540, 1390, 1340, 1265, 1250, 1195, 1180, 1150, 1040, 755 cm$^{-1}$.

EXAMPLE 33

1-(1-Methyl-2-piperidyl)-1-propyl 1H-indole-3-carboxylate

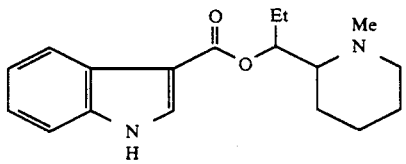

The title compound was prepared by the procedures of Example 1 using 1-(1-methyl-2-piperidyl)-1-propanol prepared in Reference Examples 5 and 6.

$^1$H-NMR(CDCl$_3$)δ 1.00(t, J=7 Hz, 3H), 1.20 (m, 2H), 1.58(m, 2H), 1.80(m, 4H), 2.20(m, 2H), 2.39(s, 3H), 2.90(m, 1H), 5.49(m, 1H), 7.26(m, 2H), 7.41(m, 1H), 7.92(d, J=3 Hz, 1H), 8.20(m, 1H), 9.30(br. s, 1H); IR(KBr, HCl$_{salt}$)3430, 3180, 1700, 1620, 1535, 1440, 1380, 1320, 1250, 1175, 1130, 1030, 760 cm$^{-1}$.

EXAMPLE 34

1-(1-Methyl-2-piperidyl)-2-methyl-1-propyl 1H-indole-3-carboxylate

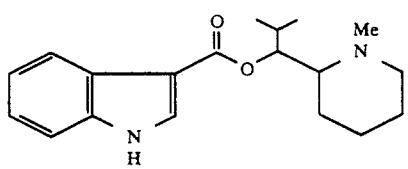

The title compound was prepared by the procedures of Example 1 wherein the reaction solvent is changed to THF: 1,3-dimethyl-2-imidazolidinone using 1-(1-methyl-2-piperidyl)-2-methyl-1-propanol prepared in Reference Examples 5 and 6.

¹H-NMR(CDCl₃)δ 1.03(d, J=7 Hz, 3H), 1.07 (d, J=7 Hz, 3H), 1.50(m, 6H), 2.17(m, 1H), 2.40(m, 1H), 2.50(s, 3H), 2.62(m, 1H), 2.96(m, 1H), 5.37(t, J=6 Hz, 1H), 7.15(m, 2H), 7.30(m, 1H), 7.80(d, J=3 Hz, 1H), 8.05 (m, 1H); IR(KBr, HCl_salt) 3425, 2970, 2700, 1700, 1530, 1442, 1376, 1342, 1318, 1250, 1170, 1130, 1030, 780 cm⁻¹.

EXAMPLE 35

1-(1-Methyl-2-piperidyl)-1-hexyl 1H-indole-3-carboxylate

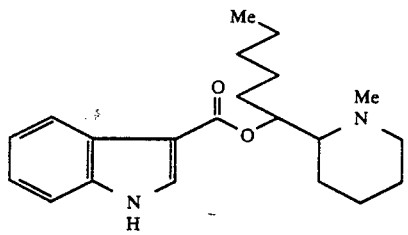

The title compound was prepared by the procedures of Example 1 using 1-(1-methyl-2-piperidyl)-1-hexanol prepared in Reference Examples 5 and 6.

¹H-NMR(CDCl₃) δ 0.84(t, J=6 Hz, 3H), 1.3 (br. m, 8H), 1.65(m, 6H), 1.97(m, 2H), 2.43(s, 3H), 3.00(br. d, 1H), 5.60(m, 1H), 7.28(m, 2H), 7.40(m, 1H), 7.94(d, J=2 Hz, 1H), 8.20(m, 1H), 9.10(br. s, 1H); IR(KBr) 3410, 3150, 2960, 2860, 1720, 1530, 1170, 1040 cm⁻¹.

EXAMPLE 36

(1,4-Dimethyl-2-piperidyl)methyl 1H-indole-3-carboxylate

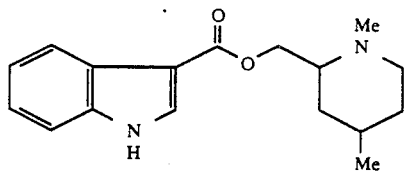

The title compound was prepared by the procedures of Example 1 using 1,4-dimethyl-2-piperidinemethanol. m.p. (HCl salt): 185° C.

¹H-NMR(CDCl₃) δ 1.20–1.97(m, 6H), 1.37 (d, J=7 Hz, 3H), 2.05–2.40(m, 2H), 2.36(s, 3H), 2.83–2.95(m, 1H), 5.56–5.68(m, 1H), 7.20–7.34(m, 2H), 7.35–7.46(m, 1H), 7.93 (d, J=3H, 1H), 8.12–8.23(m, 1H), 8.60–8.85(br., 1H); IR(KBr) 3070, 2950, 2600, 1700, 1520, 1440, 1320, 1180, 1110, 1030, 780 cm⁻¹.

EXAMPLE 37

(1,3-Dimethyl-1,2,5,6-tetrahydro-2-pyridyl)methyl 1H-indole-3-carboxylate

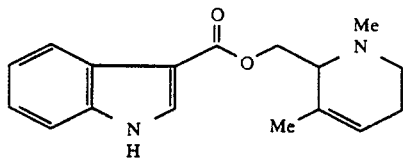

The title compound was prepared by the procedures of Example 1 using [1,3-dimethyl-2-(1,2,5,6-tetrahydropyridyl)]methanol.

m.p. 172° C.

¹H-NMR(CDCl₃)δ 1.82(s, 3H), 2.14(m, 2H), 2.55(s, 3H), 2.62(t, J=6 Hz, 1H), 2.79(t, J=6 Hz, 1H), 3.14(m, 1H), 4.39(dd, J=5 Hz, J'=12 Hz, 1H), 4.63(dd, J=3 Hz, J'=12 Hz, 1H), 5.70(br. t, 1H), 7.18(m, 2H), 7.30(m, 1H), 7.72(d, J=3 Hz, 1H), 8.11(m, 1H), 9.87(br. s, 1H); IR(KBr) 3400, 1695, 1530, 1468, 1453, 1362, 1314, 1174, 1109, 1030, 782 cm⁻¹.

EXAMPLE 38

(1,5-Dimethyl-2-piperidyl)methyl 1H-indole-3-carboxylate

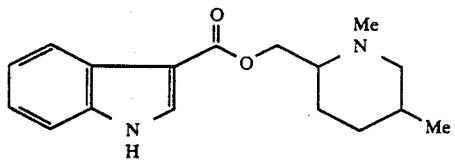

The title compound was prepared by the procedures of Example 1 using 1,5-dimethyl-2-piperidinemethanol.

¹H-NMR(CDCl₃)δ 0.99(d, J=7 Hz, 3H), 1.13–2.00(m, 5H), 2.30–2.57(m, 2H), 2.48(s, 3H), 2.78–2.95(m, 1H), 4.40(dd, J=6 Hz, J'=11 Hz, 1H), 4.56(dd, J=5 Hz, J'=11 Hz, 1H), 7.17–7.31(m, 2H), 7.31–7.46(m, 1H), 7.87–7.93(m, 1H), 8.14–8.26(m, 1H), 8.75–8.98(br., 1H).

EXAMPLE 39

(1,3-Dimethyl-2-piperidyl)methyl 1H-indole-3-carboxylate

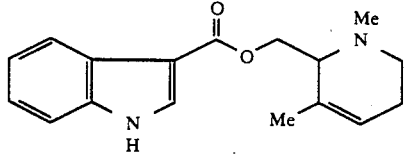

The title compound was prepared by the procedures of Example 1 using 1,3-dimethyl-2-piperidinemethanol.

¹H-NMR(CDCl₃)δ 1.06(d, J=7 Hz, 3H), 1.35–2.16(m, 5H), 2.16–2.32(m, 1H), 2.41(s, 3H), 2.56–2.81(m, 2H), 4.36(dd, J=5 Hz, J'=12 Hz, 1H), 4.53(dd, J=6 Hz, J'=12 Hz, 1H), 7.20–7.34(m, 2H), 7.34–7.46(m, 1H), 7.90 (d, J=2 Hz, 1H), 8.15–8.24(m, 1H), 8.75–8.93(br., 1H).

EXAMPLE 40

(1-Methyl-2-hexahydroazepinyl)methyl 1H-indole-3-carboxylate

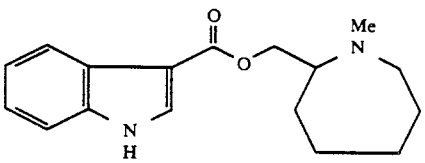

The title compound was prepared by the procedures of Example 1 using (1-methyl-2-hexahydroazepinyl)methanol.

¹H-NMR (CDCl₃)δ 1.35–2.00(m, 8H), 2.55 (s, 3H), 2.75–3.07(m, 3H), 4.15(dd, J=7 Hz, J'=11 Hz, 1H), 4.39(dd, J=5 Hz, J'=11 Hz, 1H), 7.18–7.32(m, 2H), 7.32–7.45(m, 1H), 7.87 (d, J=3 Hz, 1H), 8.13–8.24(m, 1H), 8.80–9.05(br., 1H).

EXAMPLE 41

2-Pyridylmethyl 1H-indole-3-carboxylate

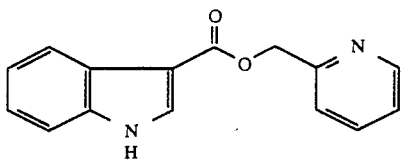

The title compound was prepared by the procedures of Example 1 using 2-pyridylmethanol.

$^1$H-NMR (CDCl$_3$)δ 5.52(s, 2H), 7.20–7.30 (m, 3H), 7.32–7.46(m, 1H), 7.51(d, J=8 Hz, 1H), 7.72(dt, J=1 Hz, J'=8 Hz, 1H), 7.98(d, J=3 Hz, 1H), 8.17–8.26(m, 1H), 8.63(d, J=5 Hz, 1H), 9.13–9.30(br., 1H).

EXAMPLE 42

4-Pyridylmethyl 1H-indole-3-carboxylate

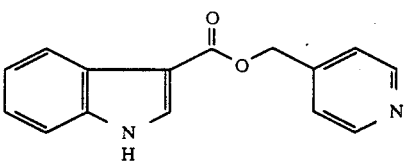

The title compound was prepared by the procedures of Example 1 using 4-pyridinemethanol.

$^1$-NMR (DMSO-d$_6$ -CDCl$_3$) δ 5.38(s, 1H), 7.10–7.27(m, 1H), 7.44(d, J=5 Hz, 2H), 7.42–7.55(m, 1H), 7.94–8.07(m, 1H), 8.13–8.21(m, 1H), 8.57(d, J=5 Hz, 2H), 11.90–12.12(br., 1H).

EXAMPLE 43

(S)-(−)-(1-Methyl-2-piperidyl)methyl 1H-indole-3-carboxylate

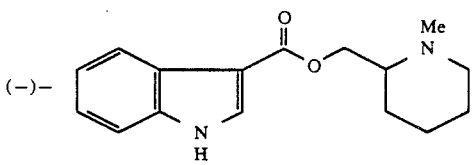

The title compound was prepared by the procedures of Example 1 using (−)-(1-methyl-2-piperidine)methanol as prepared in Reference Example 7.

[α]$_D$ −34.8° (c=1.06, CHCl$_3$).

EXAMPLE 44

(R)-(+)-(1-Methyl-2-piperidyl)methyl 1H-indole-3-carboxylate

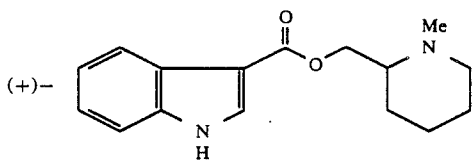

The title compound was prepared by the procedures of Example 1 using (+)-1-methyl-2-piperidinemethanol prepared in Reference Example 7.

[α]$_D$ +36.0° (c=0.60, CHCl$_3$).

EXAMPLE 45

(1S, 2'S)-(−)-1-(1-Methyl-2-piperidyl)-1-ethyl 1H-indole-3-carboxylate

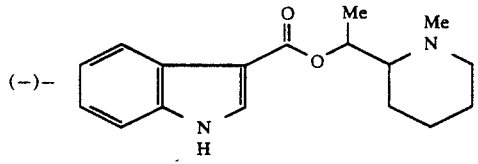

[α]$_D$ −18.4° (c=1.80, CHCl$_3$) 97% e.e. (the enantiomeric ratio was determined by high performance liquid chromatography), m.p. 143.0° C.

EXAMPLE 46

(1R,2'R)-(+)-1-(1-Methyl-2-piperidyl)-1-ethyl 1H-indole-3-carboxylate

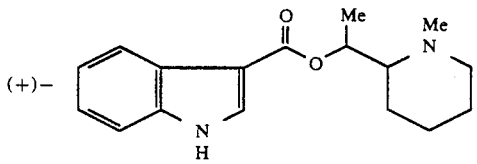

[α]$_D$ +18.9° (c=1.68, CHCl$_3$) 100% e.e. (the enantiomeric ratio was determined by high performance liquid chromatography), m.p. 143.8° C.

EXAMPLE 47

1,1-Dimethyl-2-(1H-indole-3-carbonyloxymethyl)hexahydroazepinium iodide

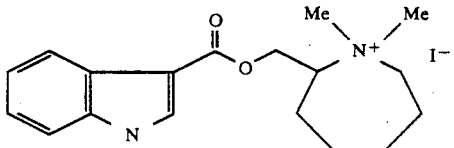

The title compound was prepared by the procedures of Example 16 using the compound prepared in Example 40.

$^1$H-NMR(DMSO-d$_6$) δ 1.35–1.72(m,2H), 1.72–2.30(m,6H), 3.15(s,3H), 3.31(s,3H), 3.40–3.80(m,2H), 3.81–4.00(m,1H), 4.47–4.66(m,1H), 4.66–4.83(1H,m), 7.05–7.32(m,2H), 7.44–7.58(m,1H), 7.93–8.07(m,1H), 8.07–8.22(m,1H), 11.90–12.08(br.,1H).

EXAMPLE 48

1,1-Dimethyl-2-(1H-indole-3-carbonyloxymethyl)-piperidinium bromide

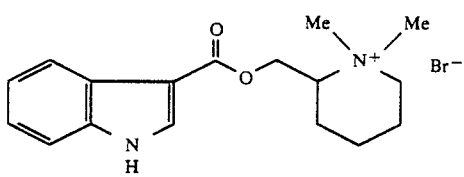

The title compound was prepared by the procedures of Example 16 using the compound prepared in Example 4, m.p. 209.1°–209.6° C.

IR(KBr) 3414, 2954, 1699, 1535, 1473, 1369, 1227, 1107, 754 cm$^{-1}$.

EXAMPLE 49

1,1-Dimethyl-2-(1H-indole-3-carbonyloxy-1-ethyl)-piperidinium iodide

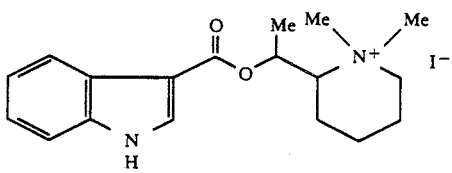

The title compound was prepared by the procedures of Example 16 using the compound prepared in Example 28.

IR(KBr) 3428, 1698, 1528, 1429, 1312, 1241, 1172, 1057, 1023, 780 cm$^{-1}$.

EXAMPLE 50

1,1-Dimethyl-2-(1H-indole-3-carbonyloxy-1-ethyl)-piperidinium bromide

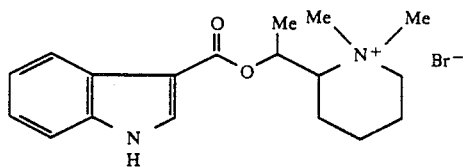

The title compound was prepared by the procedures of Example 16 using the compound prepared in Example 28.

IR(KBr) 3436, 2952, 1698, 1525, 1428, 1310, 1171, 1102, 1026, 752 cm$^{-1}$.

EXAMPLE 51

1,1-Dimethyl-2-[1-(1H-indole-3-carbonyloxy)-1-ethyl]-piperidinium bromide

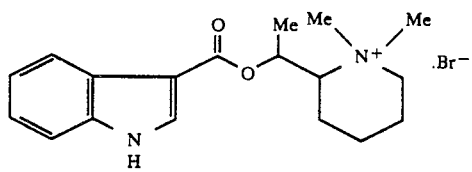

The title compound was prepared by the procedures of Example 16 using the compound prepared in Example 29, m.p. 236.1°–237° C.

IR(KBr) 3412, 3182, 1699, 1524, 1429, 1311, 1253, 1173, 1125, 1045, 782 cm$^{-1}$.

EXAMPLE 52

1,1-Dimethyl-2-(1H-indole-3-carbonyloxymethyl)-piperidinium iodide

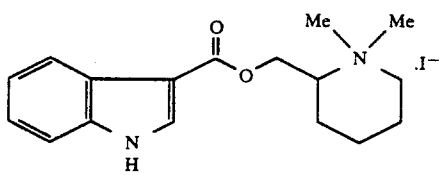

The title compound was prepared by the procedures of Example 16 using the compound prepared in Example 44, m.p. 222°–224° C.

IR(KBr) 3396, 3162, 2918, 1707, 1532, 1430, 1325, 1254, 1150, 1118, 755 cm$^{-1}$.

EXAMPLE 53

1,1-Dimethyl-2-(1H-indole-3-carbonyloxymethyl)-piperidinium bromide

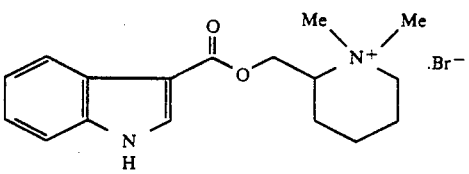

The title compound was prepared by the procedures of Example 16 using the compound prepared in Example 44, 240.2°–241.0° C.

IR(KBr) 3420, 3134, 1706, 1533, 1436, 1329, 1152, 1124, 1041, 745 cm$^{-1}$.

EXAMPLE 54

(−)-1,1-Dimethyl-2-[1-(1H-idole-3-carbonyloxy)-1-ethyl]piperidinium bromide

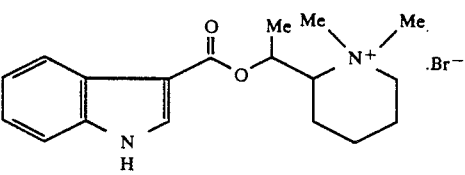

The title compound was prepared by the procedures of Example 16 using the compound prepared in Example 46.

IR(neat) 3116, 2948, 1687, 1621, 1526, 1431, 1314, 1171, 1029, 920, 757 cm$^{-1}$.

[α]$_D$ −9.1° (c=1.32, CH$_3$OH).

EXAMPLE 55

1,1-Dimethyl-2-(1H-indole-3-carbonyloxymethyl)-piperdidinium bromide

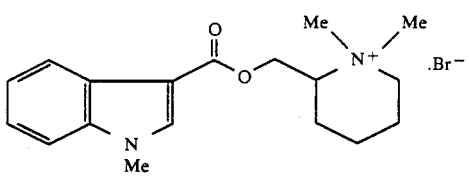

The title compound was prepared by the procedures of Example 16 using the compound prepared in Example 13.

IR(KBr) 3414, 2954, 1699, 1535, 1473, 1369, 1227, 1107, 754 cm$^{-1}$.

The preparation of the compounds used as starting material in the above examples will be given below as reference examples.

REFERENCE EXAMPLE 1

2-(tert-Butyldimethylsilyloxymethyl)piperidine

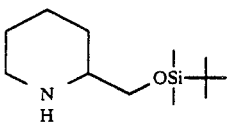

To a DMF (3 ml) solution of 2-piperidinemethanol (1.00 g, 8.7 mmol) and imidazole (1.48 g, 21.7 mmol) was added tert-butyldimethylchlorosilane (1.57 g, 10.4 mmol) at room temperature. After stirring for 30 min., a reaction solution was poured onto water followed by extraction with diethyl ether (about 30 ml). The extract was washed successively with water and saturated aqueous sodium chloride and then dried over anhydrous magnesium sulfate. The solvent was removed under reduced pressure to afford 1.61 g of the title compound.

REFERENCE EXAMPLE 2

1-Benzyl-2-(tert-butyldimethylsilyloxymethyl)piperidine

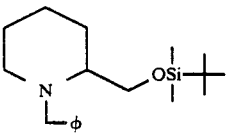

To a DMF (4 ml) solution of 60% sodium hydride (0.21 g, 5.2 mmol) was dropwise added a DMF (4 ml) solution of 2-(tert-butyldimethylsilyloxymethyl)piperidine (1.00 g, 4.4 mmol) at room temperature. The mixture was stirred at room temperature for 30 min., to which was then dropwise added a THF (1 ml) solution of benzyl bromide (0.75 g, 4.4 mmol). After stirring at room temperature for additional 30 min., a reaction solution was poured onto water followed by extraction with diethyl ether (30 ml). The extract was washed successively with water and saturated aqueous sodium chloride and then dried over anhydrous magnesium sulfate. The solvent was removed under reduced pressure to give 1.30 g of the title compound.

REFERENCE EXAMPLE 3

1-Benzyl-2-piperidinemethanol

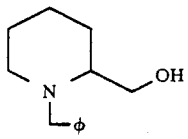

To an ice-cooled THF solution of tetrabutylammonium fluoride (1M, 3.2 ml) was dropwise added a THF (2 ml) solution of 1-benzyl-2-(tert-butyldimethylsilyloxymethyl)-piperidine (1.00 g, 3.2 mmol). After stirring at room temperature for 2 hours, a reaction solution was poured onto water followed by extraction with ethyl acetate (30 ml). The extract was washed successively with water and saturated aqueous sodium chloride and then dried over anhydrous magnesium sulfate. The solvent was removed under reduced pressure. The crude product thus obtained was purified by a column chromatography on silica gel (SiO$_2$: 20 g, CHCl$_3$) to afford 0.41 g of the title compound.

REFERENCE EXAMPLE 4

1-(2-Propyl)-2-piperidinemethanol

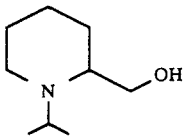

In a closed stainless steel tube were heated pyridine-2-methanol (3.27 g, 30 mmol) and 2-iodopropane (3.59 ml, 36 mmol) at 120° C. for 20 hours. A reaction product was dissolved in a methanol-water (10:1) mixture 23 ml) followed by addition of sodium borohydride (1.14 g, 30 mmol). After stirring at room temperature for 3 hours, a reaction solution was concentrated to dryness. To the residue was added water followed by extraction with ethyl acetate. The organic layer was dried over anhydrous magnesium sulfate, and the solvent was removed under reduced pressure. The crude product thus obtained was purified by column chromatography on silica gel (SiO$_2$: 90 g, CHCl$_3$) to give 0.61 g of a product (yield 13%). The substance was then subjected to catalytic hydrogenation (2.7 kg/cm$^2$, 1 hour) at room temperature in ethanol (20 ml) using platinum oxide (0.07 g) as a catalyst. The catalyst was removed by filtration, and the filtrate was concentrated under reduced pressure to give 0.58 g of the title compound.

REFERENCE EXAMPLE 5

Phenyl(2-pyridyl)methanol

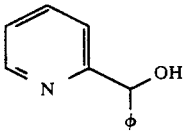

To a THF (10 ml) solution of 2-pyridinecarboxyaldehyde (0.50 g, 4.7 mmol) was slowly added a 3.0M ether solution of phenylmagnesium bromide (2.6 ml, 7.8 mmol) at room temperature. After stirring for 1 hour, to a reaction solution was slowly added diluted aqueous hydrochloric acid drop by drop. The organic layer was separated, and the aqueous layer was extracted with ether. The combined organic layer was washed with saturated aqueous sodium chloride and then dried over anhydrous magnesium sulfate. The solvent was removed under reduced pressure to give a crude product, which was purified by column chromatography on silica gel (SiO$_2$: 50 g, ethyl acetate:hexane=1:1). Then, the desired fraction was distilled under reduced pressure to afford the title compound (0.84 g). The product crystallized at room temperature.

b.p. 104°–109° C. (0.25 mmHg).

m.p. 63°–54° C.

$^1$H-NMR(CDCl$_3$)δ5.31(br. s, 1H), 5.75(s, 1H), 7.1–7.4(m, 7H), 7.61(dd, J=8 Hz, J'=1 Hz, 1H), 8.56(d, J=5 Hz, 1H).

REFERENCE EXAMPLE 6

Phenyl[2-(1-methylpiperidyl)]methanol

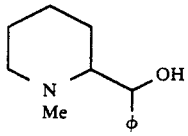

A mixture of phenyl(2-pyridyl)methanol (6.24 g, 33.7 mmol) and iodomethane (8.00 g, 56.3 mmol) was reacted in a closed stainless steel tube at 110° C. for 1 hour. To a solution of the reaction product in methanol (100 ml) was slowly added sodium borohydride (7.65 g, 0.20 mol). The mixture was stirred at room temperature for 2 hours, and the solvent was then removed under reduced pressure. To the residue was added water followed by extraction with ether. The organic layer was washed with saturated aqueous sodium chloride and dried over anhydrous magnesium sulfate. The solvent was removed under reduced pressure to give a product as a brown oil. Subsequently, the oil was dissolved in ethanol (100 ml) followed by addition of platinum oxide (0.23 g). The mixture was subjected to catalytic hydrogenation (hydrogen pressure: 3 kg/cm$^2$) at room temperature. The reaction solution was filtered, and the filtrate was concentrated under reduced pressure to give the title compound (2.00 g).

REFERENCE EXAMPLE 7

Preparation of Both Enantiomers of 1-methyl-2-piperidinemethanol

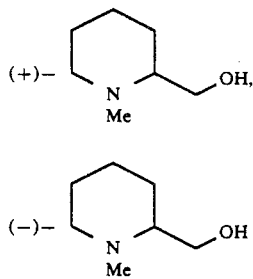

A mixture of 1-methyl-2-piperidinemethanol (48.8 g, 0.378 mol) and dibenzoyl-D-tartaric acid monohydrate (130.0 g, 0.363 mol) was dissolved in ethanol (200 ml) with heating. Additional ethanol (50 ml) was added, and the mixture was stirred under ice-cooling. Crystallization occurred. After stirring for 3 hours crystals precipitated were filtered, washed with cold ethanol and air dried. A pale brown solid thus produced (73.4 g) was dissolved in ethanol (160 ml) with heating. The solution was stirred at room temperature to effect recrystallization. Crystals precipitated were filtered, washed with cold ethanol and then dried in vacuum (50° C.) to give pale yellow crystals (52.3 g, 59%). Specific rotation of the product was [α]$_D$ +90° (c=1.02, MeOH). The crystals were dissolved in 3N aqueous hydrochloric acid (200 ml), and the solution was washed with ethyl acetate (2×200 ml). The aqueous layers were adjusted with powdery sodium carbonate to a pH >10, and then was concentrated under reduced pressure. The residue was extracted with chloroform (2×300 ml), and the extracts were dried over anhydrous magnesium sulfate. The solvent was distilled off under reduced pressure. (+) Enantiomer of the title compound (8.68 g, yield 64%) was produced as a pale yellow oil. [α]$_D$ +33.4° (c=1.67, MeOH).

The (−) enantiomer produced in the same way as above using dibenzoyl-L-tartaric acid. [α]$_D$ −34.7° (c=1.47, MeOH).

REFERENCE EXAMPLE 8

Preparation of both enantiomers of 1-methyl-2-piperidine-1-ethanol

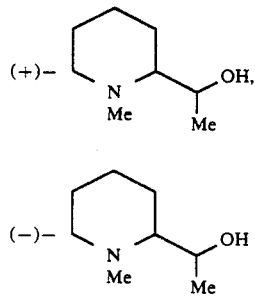

To a dichloromethane (75 ml) solution of oxalyl chloride (3.04 ml, 33.9 mmol) cooled to −78° C. was slowly added dropwise a dichloromethane (15 ml) solution of DMSO (5.2 ml, 67.8 mmol). Then, a dichloromethane (30 ml) solution of (−)-1-methyl-2-piperidinemethanol (3.04 g, 23.8 mmol) produced in Reference Example 7 was dropwise added, and the mixture was stirred at −78° C. for 30 min. Triethylamine (22 ml, 150 mmol) was slowly dropped, and the mixture was stirred for 15 min. Temperature of the resulting mixture was raised to approximately 10° C. followed by addition of water (65 ml). The organic layer was separated, and the aqueous layer was extracted with chloroform (2×100 ml). The combined organic layers were washed with saturated aqueous sodium chloride and dried over anhydrous magnesium sulfate. The solvent was removed under reduced pressure to give a crude product as a brown oil (3.00 g). The crude aldehyde thus obtained was used immediately in the next step without any further purification.

To a solution of the crude aldehyde (3.00 g, 33.8 mmol) in ether (100 ml) was dropwise added under ice-cooling a 1.0M ether solution of methylmagnesium iodide (25 ml, 25 mmol). Subsequently, the mixture was stirred at room temperature for 2 hours followed by addition of a saturated aqueous ammonium chloride (50 ml). The mixture was extracted with chloroform (2×100 ml), and the organic layers were washed with saturated aqueous sodium chloride and dried over anhydrous magnesium sulfate. The solvent was removed by distillation under reduced pressure, and a crude product was distilled under reduced pressure to afford the (−) enantiomer of the title compound (1.04 g).

b.p. 95°–96° C. (18 mHg).

$[\alpha]_D$ −18.5° (c=2.05, CHCl$_3$). (79% e.e. by HPLC).

EXAMPLE 56

The compounds prepared in the above examples were respectively tested for antagonism of 5-HT at 5HT$_3$ receptors.

Administration of 5-HT (serotonin) to anesthesized rats via jugular vein induces temporary bradycardia (von Bezold Jarisch Reflex) (A. S. Paintal, Physiol. Rev., 53, 159–227 (1973)). It is demonstrated by Richardson et al. (Nature, 316, 126–131 (1985)) that the 5-HT-induced reflex is produced via 5-HT$_3$ receptors. Accordingly, an effective and selective antagonism of 5-HT at 5-HT$_3$ receptors by a compound of the invention, if any, could be demonstrated by inhibition of said reflex.

Thus, rats were anesthesized with urethane (1 g/kg, i.p.) and recorded for blood pressure and heart rate from left femoral artery. Percent inhibition was calculated from bradycardia induced by 5-HT (30 μg/kg) given 5 min. following intrajugular administration of a compound of the invention, taking the bradycardia induced by the intrajugular administration of 5-HT. The percent inhibition is listed in the table below.

In this test, all of the test compounds were tested in the form of hydrochloride except for the compounds prepared by the procedures of Example 16 (quaternary ammonium salt). Therefore, concentration of the test drug is expressed in terms of the concentration of the hydrochloride except for the compounds prepared by the procedures of Example 16. The compound produced in Example 15 was tested in the form of dihydrochloride.

| | Antagonism of 5-HT$_3$ | | |
|---|---|---|---|
| | Concentration of test drug (μg/kg, i.v.) | | |
| Example No. | 10 | 100 | 1000 |
| 1 | | | 64 |
| 2 | | | 78 |
| 3 | | | 28 |
| 4 | 36 | 85 | |
| 5 | | | 81 |
| 6 | | | 23 |
| 7 | | 19 | |
| 8 | | 19 | |
| 9 | | | 16 |
| 10 | | 12 | |
| 11 | | 16 | |
| 12 | | 15 | |
| 13 | 26 | 65 | |
| 15 | | | 37 |
| 16 | 52 | | |
| 17 | | 37 | 63 |
| 18 | | | 52 |
| 19 | 33 | 76 | |
| 20 | | | 94 |
| 21 | | | 70 |
| 22 | 38 | 57 | |
| 23 | | 79 | |
| 25 | | 41 | |
| 27 | | 26 | |
| 28 | | 81 | |

| | -continued | | |
|---|---|---|---|
| | Antagonism of 5-HT$_3$ | | |
| | Concentration of test drug (μg/kg, i.v.) | | |
| Example No. | 10 | 100 | 1000 |
| 29 | | | 44 |
| 32 | | | 31 |
| 33 | | 21 | 51 |
| 34 | | 13 | |
| 36 | | 50 | |
| 37 | | 17 | |
| 38 | | 38 | |
| 39 | 26 | 59 | |
| 40 | | 47 | |
| 41 | | 21 | |
| 42 | | 12 | |
| 43 | | 29 | 40 |
| 44 | 21 | 63 | |
| 45 | | 42 | |
| 46 | 59 | | |
| 47 | | 67 | |
| 48 | 49 | | |
| 49 | 55 | | |
| 50 | 50 | | |
| 51 | | 34 | |
| 52 | 23 | | |
| 53 | 46 | | |
| 54 | 75 | | |
| 55 | 62 | | |

The following examples illustrate pharmaceutical formulations according to the invention, in which the term "active ingredient" represents a compound of formula (I).

| Tablets (per tablet) | |
|---|---|
| Active ingredient | 10 mg |
| Lactose | 67 mg |
| Crystalline cellulose | 15 mg |
| Corn starch | 7 mg |
| Magnesium stearate | 1 mg |
| | 100 mg |

The above ingredients were uniformly blended to produce powders for direct compression. The powders were formed in a rotary tabletting machine to tablets each 6 mm in diamter and weighing 100 mg.

| Granules (per divided packet) | |
|---|---|
| Active ingredient | 10 mg |
| Lactose | 90 mg |
| Corn starch | 50 mg |
| Crystalline cellulose | 50 mg |
| Hydroxypropylcellulose | 10 mg |
| Ethanol | 9 mg |

The active ingredient, lactose, corn starch and crystalline cellulose were uniformly blended and a solution of hydroxypropylcellulose in ethanol was added. The mixture was kneaded and granulated by extrusion in a grade. The granules were then dried in a drier at 50° C. The dried granules were screened to granule sizes between 297 μm and 1460 μm to give a granule formulation weighing 200 mg per divided packet.

| Syrups | |
|---|---|
| Active ingredient | 1.000 g |
| Refined sugar | 30.000 g |
| D-Sorbitol, 70 w/v % | 25.000 g |
| Ethyl paraoxybenzoate | 0.030 g |

| Syrups | |
| --- | --- |
| Propyl paraoxybenzoate | 0.015 g |
| Flavor | 0.200 g |
| Glycerin | 0.150 g |
| 96% Ethanol | 0.500 g |
| Distilled water | q.s. |
| To a total amount of | 100 ml |

Refined sugar, D-sorbitol, methyl paraoxybenzoate, propyl paraoxybenzoate and the active ingredient were dissolved in 60 g of warm water. After cooling, glycerin and a solution of the flavor in ethanol were added. To the mixture was then added water to 100 ml.

| Injections | |
| --- | --- |
| Active ingredient | 1 mg |
| Sodium chloride | 10 mg |
| Distilled water | q.s. |
| To a total amount of | 1.0 ml |

Sodium chloride and the active ingredient were dissolved in distilled water to give a solution in a total amount of 1.0 ml.

| Suppositories | |
| --- | --- |
| Active ingredient | 2 g |
| Polyethylene glycol 4000 | 20 g |
| Glycerin | 78 g |
| To a total amount of | 100 g |

Glycerin was added to the active ingredient to give a solution. To the solution was added polyethylene glycol 4000, and the mixture was warmed to give a solution. the solution was poured into suppository mold and solidified by cooling to prepare suppositories each weighing 1.5 g.

What is claimed is:

1. A compound of formula I

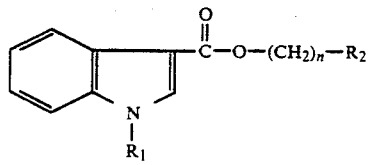

wherein $R_1$ is a hydrogen atom, a $C_1$-$C_6$ alkyl group, benzyl or an indolyl carbonyl group, $R_2$ is pyrrolidinyl, piperidyl, pyridyl, piperazinyl or hexahydroazepinyl, those heterocyclic groups are optionally substituted at an N or C atom by $C_1$-$C_6$ alkyl, benzyl or phenethyl, n is an integer of 1 to 5 and an alkylene chain —$(CH_2)_n$— is optionally substituted by $C_1$-$C_6$ alkyl, phenyl, hydroxyl or benzyl, with the proviso of excluding a compound wherein n is 1 and $R_2$ is 1-methyl-2-pyrrolidinyl or 1-benzyl-2-pyrrolidinyl, or a physiologically acceptable salt or quaternary ammonium salt thereof.

2. A compound of claim 1 wherein $R_1$ is hydrogen, $C_1$-$C_5$ alkyl, benzyl or indole-3yl carbonyl.

3. A compound of claim 1 wherein $R_2$ is pyrrolidinyl, piperidyl, pyridyl, piperazinyl or hexahydroazepinyl, which are unsubstituted.

4. A compound of claim 1 wherein $R_2$ is pyrrolidinyl, piperidyl, pyridyl, piperazinyl or hexahydroazepinyl, which are substituted at an N or C atom by $C_1$-$C_5$ alkyl, benzyl or phenethyl.

5. A compound of claim 1 wherein n is 1 to 3.

6. A compound of claim 1 wherein the alkylene chain is unsubstituted.

7. A compound of claim 1 wherein the alkylene chain is substituted by $C_1$-$C_6$ alkyl, phenyl, hydroxyl or benzyl.

8. A pharmaceutical composition for the use as selective antagonists of 5-HT at 5-$HT_3$ receptors comprising as an active ingredient an effective amount of a compound of formula I as defined in claim 1 or a physiologically acceptable salt or quaternary ammonium salt thereof together with at least one physiologically acceptable carrier or excipient.

* * * * *